United States Patent
Chang et al.

(10) Patent No.: US 10,996,172 B2
(45) Date of Patent: May 4, 2021

(54) SURFACE-FUNCTIONALIZED NANOSTRUCTURES FOR MOLECULAR SENSING APPLICATIONS

(71) Applicants: Northwestern University, Evanston, IL (US); NATIONAL INSTITUTE OF MATERIAL SCIENCE, Tsukuba (JP)

(72) Inventors: Robert P. H. Chang, Glenview, IL (US); Shiqiang Li, Clayton (AU); Peijun Guo, Woodridge, IL (US); Kai Chen, Tsukuba (JP); Keiko Okano, Tsukuba (JP); Tadaaki Nagao, Tsukuba (JP)

(73) Assignees: NATIONAL INSTITUTE OF MATERIAL SCIENCE, Tsukuba (JP); Northwestern University, Evanston, IL (US)

( * ) Notice: Subject to any disclaimer, the term of this patent is extended or adjusted under 35 U.S.C. 154(b) by 0 days.

(21) Appl. No.: 16/607,518

(22) PCT Filed: Apr. 27, 2018

(86) PCT No.: PCT/US2018/029838
§ 371 (c)(1),
(2) Date: Oct. 23, 2019

(87) PCT Pub. No.: WO2018/200982
PCT Pub. Date: Nov. 1, 2018

(65) Prior Publication Data
US 2020/0141871 A1    May 7, 2020

Related U.S. Application Data

(60) Provisional application No. 62/491,445, filed on Apr. 28, 2017.

(51) Int. Cl.
*G01N 21/65* (2006.01)
*G01N 33/58* (2006.01)

(52) U.S. Cl.
CPC ......... *G01N 21/658* (2013.01); *G01N 33/587* (2013.01); *G01N 2021/653* (2013.01)

(58) Field of Classification Search
CPC .................................................. G01N 21/658
(Continued)

(56) References Cited

U.S. PATENT DOCUMENTS 6,174,677 B1    1/2001  Vo-Dinh
7,466,406 B2   12/2008  Mirkin et al.
(Continued)

FOREIGN PATENT DOCUMENTS

WO    WO 2017/184790 A1    10/2017

OTHER PUBLICATIONS

Paramonov et al., "Theoretical Characterization of the Indium Tin Oxide Surface and of Its Binding Sites for Adsorption of Phosphonic Acid Monolayers," Chem. Mater., 2008, vol. 20, pp. 5131-5133.
(Continued)

*Primary Examiner* — Tarifur R Chowdhury
*Assistant Examiner* — Omar H Nixon
(74) *Attorney, Agent, or Firm* — Bell & Manning, LLC (57) ABSTRACT

Surface-functionalized nano structures, arrays of the nanostructures, and method for using the arrays in surfaced-enhanced spectroscopy and dielectric sensing applications, such as surface-enhanced infrared absorption spectroscopy, are provided. The nanostructures are functionalized with specific binding moieties that are bound to the nanostructures via phosphonic acid linkers.

27 Claims, 11 Drawing Sheets

(58) Field of Classification Search
USPC .......................................................... 356/301
See application file for complete search history.

(56) References Cited

U.S. PATENT DOCUMENTS

| | | | |
|---|---|---|---|
| 8,709,919 | B2 | 4/2014 | Buatier De Mongeot et al. |
| 9,691,987 | B1* | 6/2017 | Han .................... H01L 51/0012 |
| 2006/0054506 | A1 | 3/2006 | Natan et al. |
| 2006/0252065 | A1 | 11/2006 | Zhao et al. |
| 2007/0181502 | A1* | 8/2007 | Johnson ............... B01J 20/3227 |
| | | | 210/656 |
| 2009/0053391 | A1* | 2/2009 | Ludwig .................. A61L 31/10 |
| | | | 427/2.14 |
| 2009/0284829 | A1 | 11/2009 | Bower et al. |
| 2010/0308281 | A1* | 12/2010 | Zheng ................... C08L 101/10 |
| | | | 252/519.33 |
| 2013/0157254 | A1 | 6/2013 | Sengupta et al. |
| 2016/0158724 | A1* | 6/2016 | Chang .................. G01N 21/658 |
| | | | 29/458 |
| 2017/0030836 | A1 | 2/2017 | Kim |
| 2017/0221596 | A1* | 8/2017 | Caldwell ............... G01J 5/0896 |

OTHER PUBLICATIONS

Li et al., "Theoretical study of the surface modification of indium tin oxide with trifluorophenyl phosphoric acid molecules: impact of coverage density and binding geometry†‡," J. Mater. Chem., 2010, vol. 20, pp. 2630-2637.

Hoang et al., "Monitoring the Presence of Ionic Mercury in Environmental Water by Plasmon-Enhanced Infrared Spectroscopy," Scientific Reports, vol. 3, No. 1175; DOI:10.1038/srep01175 (2013), pp. 1-6.

Luis E. Oquendo Galarza, Thesis, "Modification of Indium Tin Oxide Surfaces with Phosphonic Acid Functionalized Phthalocyanines," The University of Arizona, Download date: Oct. 24, 2019, http://hdl.handle.net/10150/344225, pp. 1-218.

Koh et al., "Phenylphosphonic Acid Functionalization of Indium Tin Oxide: Surface Chemistry and Work Functions," Langmuir, 2006, vol. 22, pp. 6249-6255.

Ruan et al., "Surface-enhanced Raman spectroscopy for uranium detection and analysis in environmental samples," Analytica Chimica Acta, 2007, vol. 605, pp. 80-86.

Losego et al. "Characterizing the Molecular Order of Phosphonic Acid Self-Assembled Monolayers on Indium Tin Oxide Surfaces," Langmuir, 2011, vol. 27, pp. 11883-11888.

Brewer et al., "Formation of Thiolate and Phosphonate Adlayers on Indium-Tin Oxide: Optical and Electronic Characterization," Langmuir, 2002, vol. 18, pp. 6857-6865.

Yan et al., "Preparation and Characterization of Self-Assembled Monolayers on Indium Tin Oxide," Langmuir, 2000, vol. 16, pp. 6208-6215.

Zheng et al., "Surface Modification of Indium-Tin Oxide with Functionalized Perylene Diimides: Characterization of Orientation, Electron-Transfer Kinetics and Electronic Structure," J. Phys. Chem. C, 2016, vol. 120, pp. 20040-20048.

Hotchkiss et al., "The Modification of Indium Tin Oxide with Phosphonic Acids: Mechanism of Binding, Tuning of Surface Properties, and Potential for Use in Organic Electronic Applications," Accounts of Chemical Research, 2012, vol. 45, No. 3, pp. 337-346.

The International Search Report and Written Opinion issued in International Application No. PCT/US2018/29838 dated Jul. 11, 2018, pp. 1-10.

Adden et al., "Phosphonic Acid Monolayers for Binding of Bioactive Molecules to Titanium Surfaces," Langmuir, 2006, vol. 22, No. 19, pp. 8197-8204.

Chan et al., "Localized Surface Plasmon Resonance Spectroscopy of Triangular Aluminum Nanoparticles," J. Phys. Chem. C, 2008, vol. 112, No. 36, pp. 13958-13963. DOI: 10.1021/jp804088z.

Anker et al., "Biosensing with plasmonic nanosensors," Nature Materials, vol. 7, Jun. 2008, pp. 442-453. DOI: 10.1038/nmat2162.

Alexandra Boltasseva et al., "Low-Loss Plasmonic Metamaterials," Science, vol. 332, Jan. 21, 2011, pp. 290-291.

A.V. Kabashin et al., "Plasmonic nanorod metamaterials for biosensing," Nature Materials, vol. 8, Nov. 2009, pp. 867-871.

J. Cao et al., "Gold nanorod-based localized surface plasmon resonance biosensors: A review," Sensors and Actuators, B: Chemical, vol. 195, May, pp. 332-351. Doi: 10.1016/j.snb.2014.01.056.

Hua Qi et al., "Plasmonic Properties of Vertically Aligned Nanowire Arrays," Journal of Nanomaterials, vol. 2012, Article ID 843402, pp. 1-7. DOI:10.1155/2012/843402.

Li et al., "Infrared Plasmonics with Indium-Tin-Oxide Nanorod Arrays," ACS Nano, vol. 5, No. 11, 2011, pp. 9161-9170.

Pamela A. Mosier-Boss, "Review of SERS Substrates for Chemical Sensing," Nanomaterials, 2017, vol. 7, No. 142, pp. 1-30. DOI:10.3390/nano7060142.

Chuanmin Ruan et al., "Surface-enhanced Raman spectroscopy for uranium detection and analysis in environmental samples," Analytica Chimica Acta, vol. 605, Issue 1, Dec. 12, 2007, pp. 80-86.

Tobias W. W. MaB et al., "Incident Angle-Tuning of Infrared Antenna Array Resonances for Molecular Sensing," ACS Photonics, 2015, vol. 2, pp. 1498-1504.

Petr Fiurasek et al., "Phosphonic and Sulfonic Acid-Functionalized Gold Nanoparticles: A Solid-State NMR Study," Langmuir 2007, vol. 23, pp. 2857-2866.

Shailender Kolipaka et al., "Fabrication and characterization of an indium tin oxide-octadecanethiol-aluminum junction for molecular electronics," Appl. Phys. Lett., vol. 88, 2006, pp. 233104-1-233104-3, DOI: 10.1063/1.2205723.

Takao Ishida et al., "Surface-Conditioning Effect of Gold Substrates on Octadecanethiol Self-Assembled Monolayer Growth," Langmuir 1997, vol. 13, pp. 4638-4643.

Kenichi Ataka et al., "Surface-enhanced infrared absorption spectroscopy (SEIRAS) to probe monolayers of membrane proteins☆," Biochimica et Biophysica Acta, vol. 1828, 2013, pp. 2283-2293.

Kai Chen et al., "Infrared Aluminum Metamaterial Perfect Absorbers for Plasmon-Enhanced Infrared Spectroscopy," Adv. Funct. Mater., 2015, vol. 25, pp. 6637-6643.

\* cited by examiner

SURFACE-FUNCTIONALIZED NANOSTRUCTURES FOR MOLECULAR SENSING APPLICATIONS

CROSS-REFERENCE TO RELATED APPLICATIONS

This application is a National Stage of International Application No. PCT/US2018/029838, filed Apr. 27, 2018, which claims the benefit of U.S. Patent Application No. 62/491,445, filed Apr. 28, 2017, the contents of which are herein incorporated by reference.

REFERENCE TO GOVERNMENT RIGHTS

This invention was made with government support under DMR1121262 awarded by the National Science Foundation. The government has certain rights in the invention.

BACKGROUND

Plasmonic nanostructures and nanostructures made of high-refractive index materials afford significantly enhanced near-fields that can be exploited for ultrasensitive molecular sensing in surface-enhanced vibrational spectroscopy and dielectric sensing. Elemental gold is usually used in plasmonic biosensing due to its stability and well-established surface functionalization.

Infrared spectroscopy and Raman scattering spectroscopy are powerful tools, enabling label-free and accurate detection of chemical and biological species through the characteristic absorption bands of certain chemical bonds, which are the "fingerprints" of the molecules. However, its application for the detection of trace amounts of analytes has been hampered by the extremely small absorption signal of the molecules. A large sampling volume is required to ensure good signal-to-noise ratios, which makes studies on the molecular level extremely difficult. Surface-enhanced infrared absorption spectroscopy and surface-enhanced Raman scattering spectroscopy provide feasible routes to dramatically increase their absorption cross-sections with enhanced near-field intensities, which can come from rough surfaces, metallic nanoparticles, or lithographically defined nanostructures on the SEIRA or SERS substrates. Due to the lighting-rod effect and the excitation of surface plasmons, the metallic nanostructures, usually made of gold (Au) or silver (Ag), enable tremendous near-field enhancement around the nanostructure surfaces, preferably at sharp tips and nanogaps. In particular, periodically arranged nanoparticles fabricated by e-beam lithography (EBL) or focused-ion beam (FIB) provide better control over the spectral positions of the plasmon resonances that are preferred to overlap with the molecular vibrations.

Traditionally, Au has been widely used as a plasmonic material due to its chemical stability and well-established surface functionalization using thiolated molecules. However, Au suffers high intrinsic optical loss and its ever-growing price also poses concerns for practical applications. Unfortunately, the use of other materials, such as aluminum, copper, and titanium nitride, has been hindered due to the difficulty in functionalizing their surfaces, which are readily oxidized, making functionalization with thiolated molecules ineffective.

Most of the current plasmonic nanostructures are supported on various substrates. Therefore, their plasmon resonances, and thus their optical properties, are fixed once the nanostructures are fabricated. A variety of schemes have been proposed to tune the plasmon resonances, leading to better and more active control of the optical responses of the nanostructures, where stimuli-responsive materials are often employed to change the effective refractive indices of the surroundings of the plasmonic nanostructures. These tuning mechanisms are not straightforward and often involve complicated setup or fabrication processes.

SUMMARY

Substrates for surface-enhanced spectroscopy are provided. Also provided are methods of using the substrates in analyte sensing applications.

One embodiment of a substrate for surface-enhanced spectroscopy comprises: (a) a substrate; and (b) an array of nanostructures on the substrate. The nanostructures, which are functionalized with specific binding moieties that are bound to the nanostructures via phosphonic acid linkers, comprise an electrically conductive oxide, an electrically conductive nitride, an electrically conductive boride, an electrically conductive carbide, a non-noble metal, or a dielectric material having a high refractive index.

One embodiment of conducting surface-enhanced spectroscopy using a substrate of the type described herein includes: exposing the array of nanostructures to a sample containing, or suspected of containing, analyte molecules that undergo specific binding reactions with the specific binding moieties; irradiating the array of nanostructures with incident radiation; and measuring a signal produced by the bound analyte.

BRIEF DESCRIPTION OF THE DRAWINGS

Illustrative embodiments of the invention will hereafter be described with reference to the accompanying drawings, wherein like numerals denote like elements.

FIG. 6 shows the XPS data of different elements in the phosphonic acid. The rise of elements of P and C in the atomic concentration coincides with the decrease of O and In, suggesting that more molecules accumulated over the ITO surface. At least two hours are needed to form a good SAM layer.

DETAILED DESCRIPTION

Surface-functionalized nanostructures, arrays of the nanostructures, and methods for using the arrays in sensing applications are provided. In some embodiments of arrays, the nanostructures are plasmonic nanostructures and the sensing applications are plasmon-enhanced sensing applications, and polariton-enhanced sensing applications, such as Surface-enhanced Infrared Absorption (SEIRA) spectroscopy, Surface-enhanced Raman Scattering (SERS) spectroscopy, Surface-enhanced Resonance Raman Scattering (SERRS) spectroscopy, Surface-enhanced Hyper Raman Scattering (SEHRS) spectroscopy, Surface-enhanced Coherent Anti-Stokes Raman Scattering (SECARS) spectroscopy, Surface Plasmon-Resonance (SPR) sensing, and Surface Plasmon-Polariton (SPP) sensing.

In plasmon-enhanced spectroscopy applications, the nanostructures excite surface plasmonic fields to enhance the detection of molecules bound to the nanostructures. Arrays of the nanostructures provide angle-dependent plasmon resonances in the near- and mid-infrared range, whose position and intensity can be readily tuned by varying the angle of the incident radiation and/or the periodicity of the nanostructure array, thereby providing an easy means for selective enhancement of targeted molecular vibrations. As a result, molecular sensing with increased sensitivity, selectivity, specificity, flexibility in application, and/or low cost of implementation is enabled. Thus, this technology is well-suited for use in portable and mobile molecular sensing devices in the healthcare, environmental, and pharmaceutical industries, among others.

The nanostructure arrays are able to provide fast, real-time detection of analytes in the field and, by conducting rapid database comparisons of the detected signals, are able to provide real-time analyte identification. Such a rapid response is critical in applications such as bio-agent detection during warfare or the aftermath of a natural disaster, so that appropriate mitigating actions can be taken immediately.

The nanostructures are composed of nanostructures having specific binding moieties, such as biomolecules, bound to their surfaces. The specific binding moieties can be bound to the nanostructures via molecular linkers that have one end bound to the nanostructure surface and another end bound to a specific binding moiety, wherein the specific binding moieties are chemical moieties that are able to specifically bind to one or move other chemical moieties, such as analytes. Some embodiments of the molecular linkers include a linker portion. For example, a molecular linker may comprise a phosphonic acid molecule, as a linker portion, bound to biotin, which provides a specific binding moiety for proteins such as avidin and streptavidin. The phosphonic acid linkers may be represented by the following formula:

—R—P(OH)$_3$, wherein R represents a single bond or a spacer comprising at least a carbon and hydrogen. For example, in some embodiments, "R" is an alkyl substituent such as alkyl, alkoxyl and thioalkyl. The binding moiety can bind to the P atom of the phosphonic acid molecule via the R group, or can bond directly to the P atom. By changing the specific binding moiety, a variety of different analyte biomolecules can be bound to the plasmonic nanostructures to form biomolecule-functionalized plasmonic nanostructures. In some embodiments, the specific binding moiety is itself a biomolecule. The examples provided herein illustrate methods for binding specific moieties to nanostructures via phosphonic acid linkers. Although indium-tin-oxide nanorods are used in the examples, the methods and linker chemistry can be applied to other non-noble metal nanostructures of the types described herein, including metal oxides, non-metal oxides, and the native oxides that form on metals, non-metals, carbides, nitrides, and borides.

Examples of biomolecules that can be used as specific binding moieties include proteins, including enzymes, DNA, RNA, DNA aptamers, RNA aptamers, protein receptors, and monoclonal antibodies; and amino acids. However, the specific binding moieties need not be biomolecules. For example, crown ethers can be specific binding moieties.

The nanostructures are electrically conducting, structures having at least one nanoscale dimension—typically a dimension of 1000 nm or less, including dimensions of 500 nm or less and dimensions of 250 nm or less. Suitable nanostructures include "one-dimensional" (1D) nanostructures, including single-crystalline one-dimensional nanostructures, which are elongated nanostructures having high aspect ratios, such as nanorods, nanowires, nanofibers, and nanowhiskers. Such nanostructures can have aspect ratios of, for example, at least 5, at least 10, at least 20, or at least 100. However, nanostructures having higher or lower aspect ratios may be used. By way of illustration only, in some embodiments of the nanostructure arrays, the nanostructures have heights in the range from about 1 μm to about 10 μm and diameters in the range from about 50 to about 250 nm. In another embodiment of the nanostructure arrays, the nanostructures can be planar structures, such as disks, with aspect ratios of, for example, at least 5, at least 10, at least 20, or at least 100. The nanostructures can be grown from or assembled on a variety of substrates. In other embodiments, nanostructures having lower aspect ratios can be used. These include substantially spherical nanoparticles, disks, and thin patterned films. Methods of making disc-shaped nanostructures are described in Yokoyama, et al., J. of Sur. Sci. Soc. of Japan, 37 [8] (2016) 380. By way of illustration only, planar nanostructures intended for use in SPR sensor applications can be attached to an attenuated total reflection (ATR) prism. The nanostructures can be made by bottom-up fabrication techniques, such as growth from catalytic nanoparticles. Alternatively, they can be made by top-down lithographic techniques. Illustrative examples of lithographic patterning methods that can be used include e-beam lithography, interference lithography, and colloidal lithography. An illustrative method for bottom up growth of nanostructures is described in Dao et al., Phys. Chem. Chem. Phys. 17 [11] (2015) 7395.

Suitable nanostructure materials can include electrically conductive materials, semiconducting materials, and/or dielectric materials. These materials include: oxides and doped metal oxides, such as metal oxides (for example, $TiO_2$, $SrTiO_3$, $Ta_2O_3$, $BaTiO_3$, tin oxide, indium-tin-oxide (ITO), doped titanium oxide, doped zinc oxide and doped indium oxide); nitrides, such as metal nitrides (for example, TiN, ZrN, TaN, HfN, and doped GaN); carbides, such as metal carbides (for example, TiC, TaC, NbC, HfC, and doped SiC); borides, such as metal borides (for example, $LaB_6$, $PrB_6$, $CeB_6$, $AlB_2$, $ZrB_2$; metals, including non-noble metals, such as aluminum (Al), Fe, Ti, Ta, Pt, Ir, Cu, W, Mo, In, Sn, Zn, Ga, and magnetic elements with d-orbitals and alloys thereof); non-metals (for example, Si and Ge) and composites of two or more of these materials or composites of one or more of these materials with other materials. Suitable dopants for zinc oxide include Al, Ga, and In. Suitable dopants for titanium oxide include Nb, Ta, F, and oxygen vacancies. Suitable dopants for GaN include Si and Mg. Suitable dopants for SiC include N and B. When metal nanostructures (for example, aluminum nanostructures) are used, the molecular linkers can be bound to the native oxide (for example, aluminum oxide) that forms on the metal nanostructure surface.

Within arrays of 1D nanostructures, the 1D nanostructures can be arranged in a substantially parallel arrangement. That is, the 1D nanostructures can be aligned vertically along their long axes. It should be noted that 1D nanostructures can be considered to be aligned vertically even if they do not run absolutely parallel with one another. For example, some imperfections in the parallel alignment of the 1D nanostructures may result from limitations in the tolerance of the top-down fabrication or bottom-up growth schemes used to form the 1D nanostructures. Generally, 1D nanostructures can be considered to be vertically aligned if their long axes are aligned within ±20° and, more preferably within ±5°, within the array.

In the nanostructure arrays, the nanostructures may be arranged periodically in a variety of patterns, such as in a square lattice or a hexagonal lattice. In arrays of plasmonic nanostructures, the spacing (i.e., pitch) of the nanostructures in the array is selected such that it allows for plasmon resonance coupling between the nanostructures and provides for resonant enhancement at wavelengths in the desired region of the electromagnetic spectrum, such as the infrared region, the ultraviolet region, the visible region, or the terahertz region. For nanostructure arrays that are to be used in resonance enhanced spectroscopy applications, the selection of nanostructure material will depend on their resonance properties. For example, aluminum nanostructures can be used for ultraviolet resonance spectroscopy applications; nitrides can be used for visible resonance spectroscopy applications; oxides, such as zinc oxides, tin oxides, and indium oxides can be used for infrared resonance spectroscopy applications; and oxides, such as $TiO_2$, $SrTiO_3$, $Ta_2O_3$, $BaTiO_3$, and non-metals, such as Si and Ge, can be used for polariton sensing applications.

The nanostructures in plasmonic nanostructure arrays generally have width dimensions and/or spacings that are smaller than the wavelengths of the incident radiation that excites the plasmon resonance. By way of illustration only, some embodiments of the arrays are composed of a periodic lattice of nanorods in a vertical arrangement with a pitch in the range from about 400 nm to 800 nm. In some embodiments, the arrays include regions with different nanostructure pitches, and/or the collection of nanostructures includes nanostructures having different heights in order to increase the number of available resonances and provide tuning capabilities in surface-enhanced spectroscopy. Regular periodic arrays of the nanostructures can be used to provide angle-dependent plasmon resonances with an extra-photonic resonance to produce sharp resonance peaks, as illustrated in the Example below. However, the nanostructures need not be arranged in a regular periodic array. Instead they can be vertically aligned with a non-periodic, random pattern on a substrate. For the purpose of this disclosure, such irregular, non-periodic arrays are referred to as nanostructure ensembles. Nanostructure ensembles give rise to plasmon resonances with broad peaks in the angle-dependent and spectral peaks.

The substrates upon which the nanostructure arrays are disposed can be, for example, yttria stabilized zirconia (YSZ), barium fluoride, calcium fluoride, diamond, germanium, alumina, silver halide, quartz, zinc serenade, silicon, alkali halide, chalcogenide glass, and thallium brom-iodide. However, other substrates can be used.

Figure 1A:
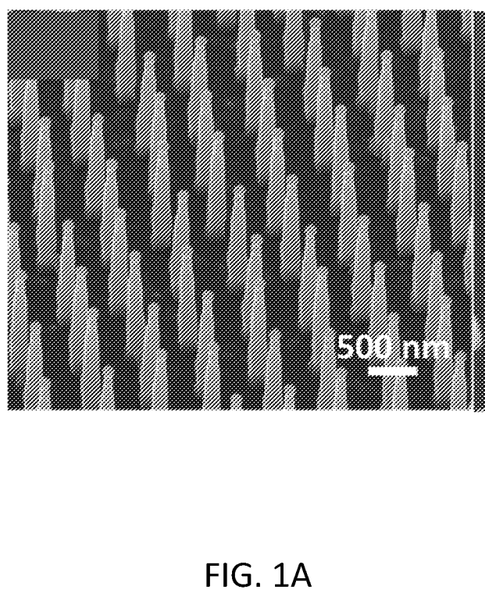
FIG. 1A is an SEM image of ITO nanorod arrays in side view.
Figure 1B:
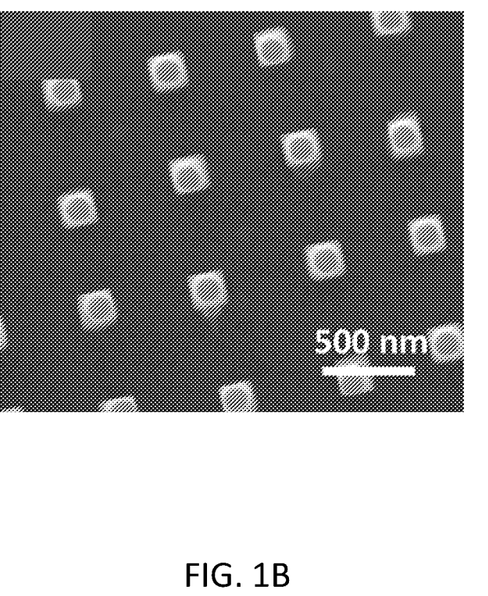
FIG. 1B is an SEM image of ITO nanorod arrays in top view. The substrate was tilted 30° from horizontal in FIG. 1A.
Figure 1C:
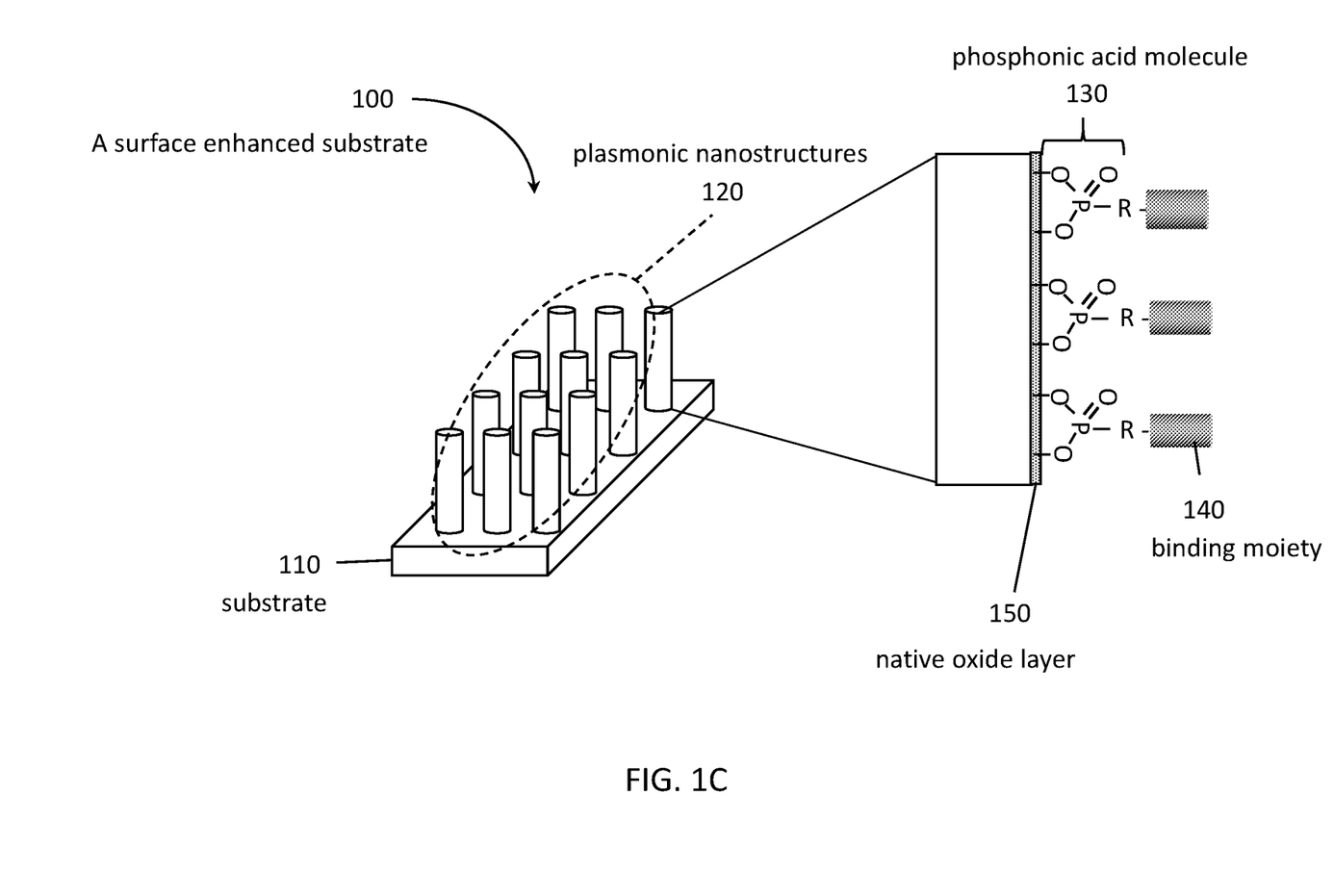
FIG. 1C is a schematic diagram showing a structure that includes an array of 1D nanostructures in a regular periodic arrangement on a substrate.

A schematic diagram showing a structure 100 that includes an array of 1D nanostructures 120 in a regular periodic arrangement on a substrate 110 is provided in FIG. 1C. In this embodiment, the specific binding moieties 140 are attached to the nanostructures 120 via phosphonic acid molecular linkers 130. Optionally, as shown here, molecular linkers 130 may be bonded to a native oxide 150 formed on the surfaces of nanostructures 120.

Surface-enhanced infrared absorption spectroscopy can be used to sense analyte biomolecules by exposing an array of plasmonic nanostructures functionalized with specific binding moieties to a sample comprising biomolecules that specifically bind to the specific binding moieties. The resulting biomolecule-functionalized plasmonic nanostructures are then irradiated with infrared incident radiation, and a plasmon-enhanced output signal is measured, wherein the output signal will have a frequency shift and/or phase change relative to the incident radiation. Samples include gaseous samples containing gaseous analytes and liquid samples, such as aqueous samples, comprising, for example, ionic analytes. Suitable light sources include lasers, light-emitting diodes, and white lights. In some embodiments, the incident radiation is, or includes, mid-infrared radiation having wavelengths in the range from 3 µm to 40 µm and/or near-infrared radiation (NIR) having wavelengths in the range from about 0.75 µm to about 3 µm, since mid-infrared radiation and NIR are useful for the detection of various biomolecules.

Depending upon the type of spectroscopy being carried out, the signal may be a radiation absorption signal, a radiation reflection signal, a radiation transmission signal, or a radiation scattering signal. That is—the signal may be collected as an absorbance spectrum, a reflectance spectrum, a transmittance spectrum, or a scattering spectrum. In some embodiments of the methods, a plasmon-enhanced signal is measured for incident radiation striking the surface at two or more different incident angles and the signals are compared.

Once the signals are collected, they can be compared to a pre-existing database of signals for known analytes, wherein matching the collected signals to one or more database signals provides an identification of the analytes. For example, a pre-existing database can include absorbance, reflection, transmission, and/or scattering spectra for various known analytes or mixtures of analytes. Moreover, these spectra can include incident angle dependent data, output angle dependent data, analyte concentration dependent data, and/or measurement time dependent data.

The arrays may be provided in the form of small chips that can be readily scattered over a large surface area, such as a battlefield, to provide real-time analyte sensing. For example, the chips may have width dimensions in the range from about 0.5 cm to 25 cm, although dimensions outside of this range could also be used. In such applications, an incident light source, such as a laser, could be directed at the sensor chips from a remote location. The light source could then scan the area and the plasmon-enhance signals from the various sensor chips can be collected for database analysis. This would allow for real-time identification of harmful analytes and a quick and appropriate response.

In SEIRA spectroscopy, an array of the biomolecule-functionalized plasmonic nanostructures is irradiated with infrared incident radiation. The biomolecules functionalizing the plasmonic nanostructures absorb a portion of the incident radiation and a resulting signal is produced. This signal may take a variety of forms, including an absorbance spectrum, a reflectance spectrum, or a transmittance spectrum. In some embodiments of the method, the incident radiation and the emitted signal are both in the infrared region of the electromagnetic spectrum. As a result of the plasmonic resonance of the nanostructures, the signal is enhanced (i.e., improved; e.g., amplified) with respect to an analogous signal obtained without the plasmonic nanostructures. Notably, because the resonance intensity varies as a function of the angle of incidence for the incident radiation, varying the incident angle provides an effective method to tune the frequencies of the plasmon resonances of the nanostructure array.

Although the SEIRA-based sensing method discussed above uses infrared radiation, some embodiments of the plasmonic nanostructures are plasmonic in the visible and/or infrared regions of the electromagnetic spectrum and, therefore, visible and/or ultraviolet radiation can also be used as the incident, exciting radiation. For example, the biomolecule-functionalized plasmonic nanostructures can be used in SERS, wherein the array of biomolecule-functionalized plasmonic nanostructures is irradiated with incident radiation and a Raman scattering signal from the biomolecules is measured, the Raman scattering signal being enhanced by the plasmonic resonance of the plasmonic nanostructures. The biomolecule-functionalized plasmonic nanostructures also can be used in SPR sensing. SPR sensing sensitively detects the dielectric function change due to the adsorption of target analytes (such as, proteins, DNA, and/or toxic ions) onto the molecular linkers. In SPR sensing, the array of biomolecule-functionalized plasmonic nanostructures is irradiated with incident radiation, and a change in the reflection angle and/or intensity of the reflected radiation is measured, using an attenuated total reflection (ATR) geometry. The biomolecule-functionalized plasmonic nanostructures also can be used in SERS sensing where the enhanced signal of Raman scattering is observed by the increased cross sections for the Raman scattering, SEERS, SEHRS, SECARS, are embodied by the presence of the electromagnetic near-field in the plasmonic nanostructures.

Alternatively, the biomolecule-functionalized plasmonic nanostructures can be used in plasmon-enhanced fluorescent spectroscopy. In plasmon-enhanced fluorescent spectroscopy, the array of biomolecule-functionalized plasmonic nanostructures is irradiated with incident radiation, and a fluorescence signal from the biomolecules is measured, wherein the fluorescence signal is enhanced by a plasmonic resonance of the plasmonic nanostructures. In plasmon-enhanced fluorescent spectroscopy, the biomolecules being detected may be fluorescent biomolecules or may be labeled with fluorescent tags.

Types of biomolecules that can be sensed using the present methods include oligonucleotide sequences, including both DNA and RNA sequences, amino acid sequences, proteins, protein fragments, ligands, receptors, receptor fragments, antibodies, antibody fragments, antigens, antigen fragments, enzymes, and enzyme fragments. In addition, although embodiments of the nanostructures used in the methods and sensors are illustrated above as "biomolecule-functionalized," the nanostructures can be functionalized with non-biological molecules and, therefore, may be more generally described as chemically functionalized. In some embodiments of the methods and sensors, the analytes being detected are not biomolecules. For example, the molecules being detected can be metal ions, such as mercury ions, cesium ions, tin ions, cadmium ions, and arsenic ions.

Table 1 lists some exemplary specific binding moiety/analyte molecule pairs.

TABLE 1

| | Binding moiety | Target substance |
| --- | --- | --- |
| 1 | Biotin | Streptavidin |
| 2 | TBA 15 DNA Aptamer | Thrombin |
| 3 | Crown Ether | Metal Ions |
| 4 | Glutathione (GSH) | $Hg^{2+}$ |
| 5 | Single-Stranded (ss) DNA | ss DNA with Complementary Bases |
| 6 | ss DNA | ss PNA with Complementary Bases |
| 7 | Dioxin | Complementary Antigen to the Dioxin |
| 8 | DNA with Thymine Bases | $Hg^{2+}$ |

EXAMPLE

This example illustrates the application of protein-functionalized single-crystalline indium-tin oxide (ITO) nanorod arrays for biosensing in infrared spectroscopy. The ITO nanorod arrays show angle-dependent plasmon resonances in the mid-infrared range, whose position and intensity can be readily tuned by varying the incident angle, thereby providing an easy means for selective enhancement of targeted molecular vibrations. The use of phosphonic-acid-derived biotin molecules to chemically functionalize the antennas, and subsequently demonstrated the specific adsorption of streptavidin onto them, was examined. The successful surface functionalization of the ITO nanorods demonstrated here facilitated the detection of functional biomolecules and proteins with high specificity.

Here, arrays of single-crystalline ITO nanorod antennas that show two resonance modes in the infrared range were investigated. The 3D vertical nanorods enabled better optical properties and more accessible enhanced near-field and provided a better platform for sensing applications. The two resonance modes could be tuned by the incident angle, and thus offered selective enhancement of certain molecular vibrations. The use of phosphonic-acid-derived biotin molecules as the self-assembled linker molecules for functionalizing the ITO antenna arrays was also demonstrated. The monolayer functionalization with phosphonic acid molecules was confirmed, as well as the subsequent attachment of streptavidin molecules onto the antennas by infrared spectroscopy and X-ray photoelectron spectroscopy.

FIG. 1 displays typical SEM images of a fabricated ITO nanorod array. Each individual ITO nanorod had a square-shaped cross-section with decreasing side-length from 180 nm at the base to 100 nm at the top. The round objects on the tips of the nanorods were the gold nanoparticles serving as the seeds for the ITO nanorod growth. The presence of these Au nanoparticles was expected to have a negligible effect on the infrared plasmon resonances of the ITO nanorods because their resonances were in the visible region due to their small size (~100 nm in diameter). The ITO nanorods were ~1.8 μm in height and were arranged in a square lattice with a pitch size of 600 nm.

Figures 2A, 2B:
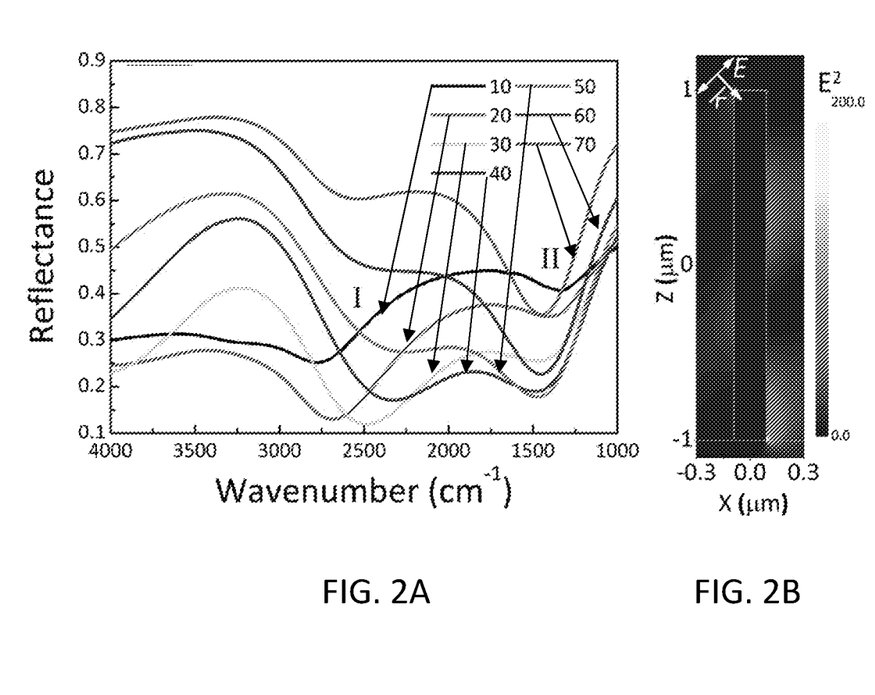
FIG. 2A shows experimental reflectance spectra of the ITO nanorod array at different incident angles. The ITO nanorod array shows two plasmon modes that are tunable under different incident angles.
FIG. 2B shows that numerical simulations of the near-field intensity profile indicate the two modes correspond to two different longitudinal modes along the ITO nanorod at 2500 $cm^{-1}$ for mode I.
Figure 2C:
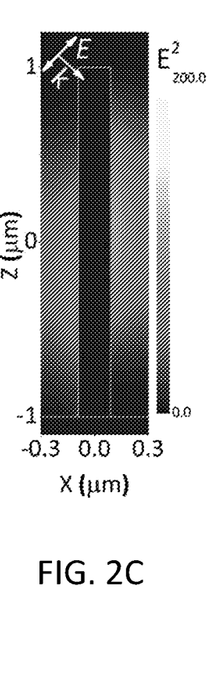
FIG. 2C shows that numerical simulations of the near-field intensity profile indicate the two modes correspond to two different longitudinal modes along the ITO nanorod at 1500 $cm^{-1}$ for mode II. The incident angles are 50° for both cases.
Figure 5:
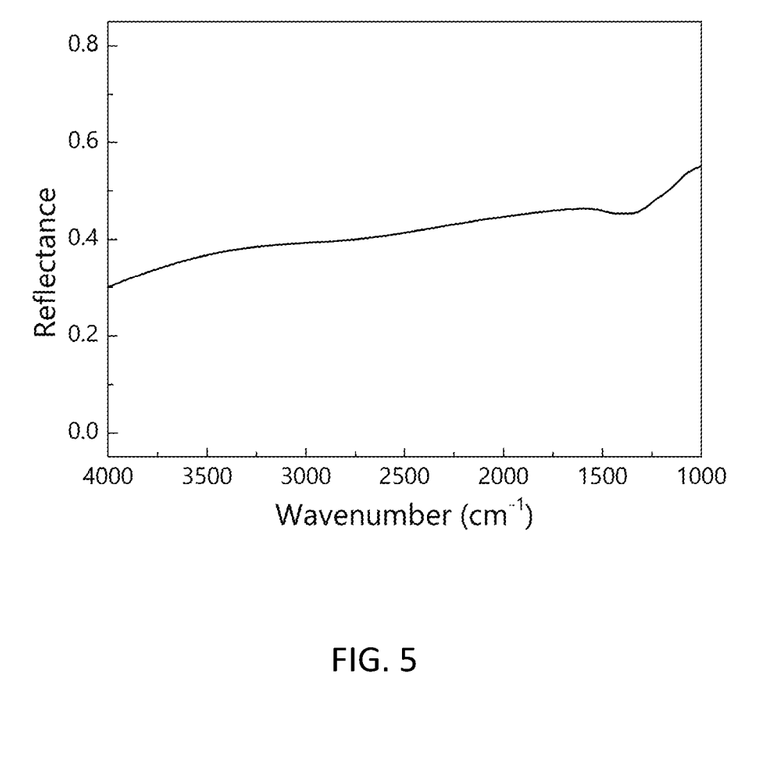
FIG. 5 depicts the reflectance spectrum of the ITO nanorod arrays with s-polarization and incident angle of 50°. The longitudinal modes of the ITO nanorods can only be excited with p-polarized light, and no modes were observed in this range.

As shown below, selective excitation and tuning of two resonance modes supported by the ITO nanorod array was demonstrated. FIG. 2A shows the experimental reflectance spectra from the ITO nanorod array under different incident angles. The incident light was set to be p-polarized, as the spectrum from s-polarization exhibited no features in the same range (FIG. 5). Reflectance from a gold mirror (100 nm in thickness) was used as reference. In general, two plasmon modes were observed under all incident angles with varying resonance positions and intensities: mode I at a higher wavenumber, and mode II at lower wavenumber. At small incident angles, mode I showed stronger resonance. As the incident angle increased, this mode becomes weaker, as manifested by the shallower dips on the spectra while mode II becomes stronger. The two modes showed similar resonance intensity when the incident angle is 40°. Numerical simulations, as shown in FIGS. 2B and 2C, indicated that the two resonances could be attributed to the different order of longitudinal modes along the ITO nanorods. The fact that these two modes could only be excited by p-polarized light also suggests the longitudinal nature of the modes. It is noted that coupling between the adjacent ITO nanorods was expected to occur in such dense arrays (the pitch of the array is 600 nm). As the incident angle changed, the coupling strength varied, leading to a change in the resonance intensity. In addition, the excitation beam was focused onto the ITO nanorod arrays in the experiments, and therefore the observed spectra carried spectra features averaged from different angles, making the two modes more complicated than the longitudinal modes in a single nanorod.

Figure 3:
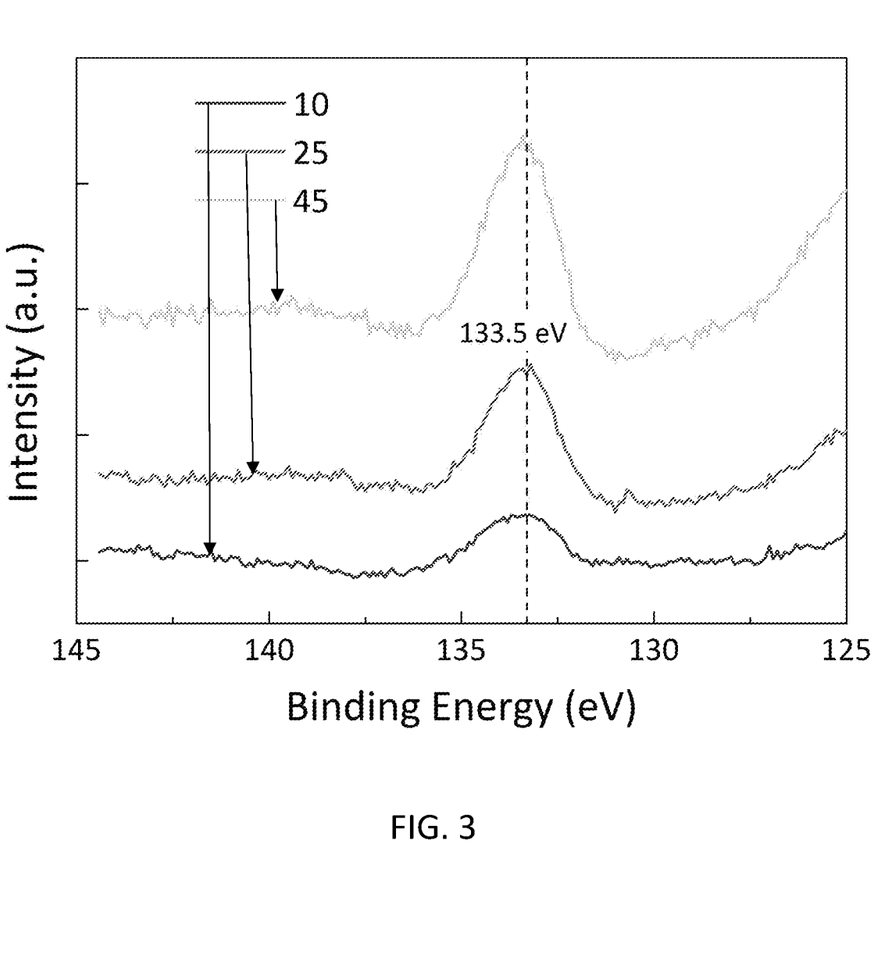
FIG. 3 depicts XPS spectra of the P2p peak from the phosphonic acid attached to the planar ITO thin films.

Reliable surface functionalization of the plasmonic nanostructures played an important role for their sensing applications. Modifying the nanostructure surfaces with functional molecules facilitated the sensing of the target analytes. Here, phosphonic-acid-derived biotin molecules were applied to functionalize the ITO nanorod surfaces. Before the SEIRA measurements, the binding of the molecules to planar ITO films was characterized with XPS. FIG. 3 shows the P2p peaks under different electron takeoff angles from the planar ITO substrates. The presence of the P2p indicated the existence of phosphonic acid molecules on the ITO surfaces and the peak position suggested the bonding state of phosphor was $PO_3$, which can bond with the metal elements in ITO. The peak intensity changes with variable takeoff angles were also investigated. The sampling depth increased as the takeoff angle increased. Therefore, the P2p peak intensity increased with larger angles, as shown in FIG. 3. In addition, the appearance of the peak even at a small takeoff angle of 10° (the sampling depth was ~1 nm) indicated that the molecules do not stand vertically on the surface, but rather are tilted, which generally happens for self-assembly monolayers (SAMs).

Figure 6:
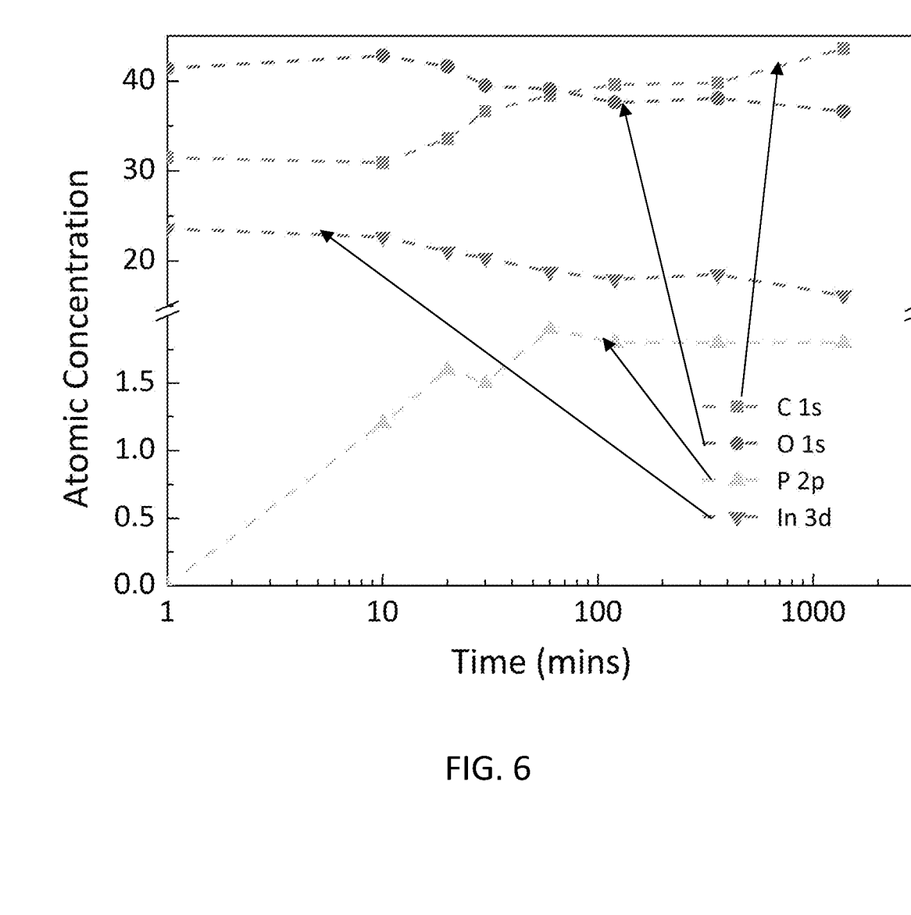

In addition, XPS data of different elements from the phosphonic acid indicated that a period of at least two hours was desirable to form a good self-assembled monolayer (SAM) on the ITO surfaces (FIG. 6). In these experiments, an incubation time of 24 hours was chosen.

Figure 7A:
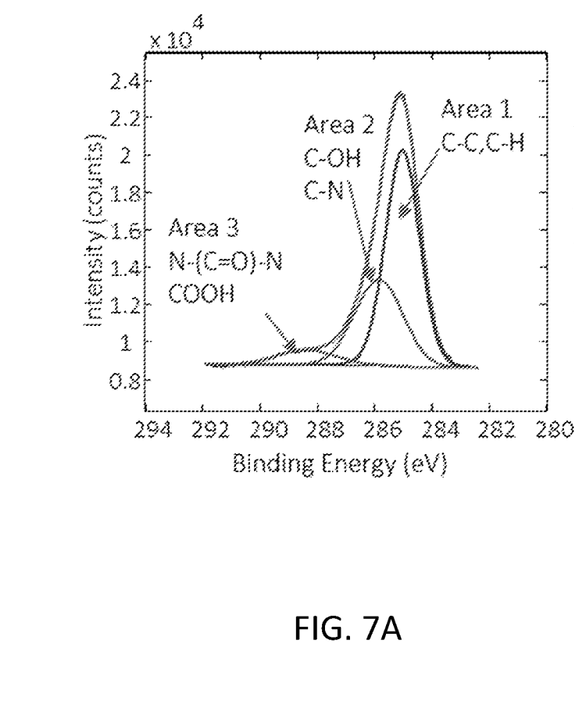
FIG. 7A shows the C1s after biotin functionalization.
Figure 7B:
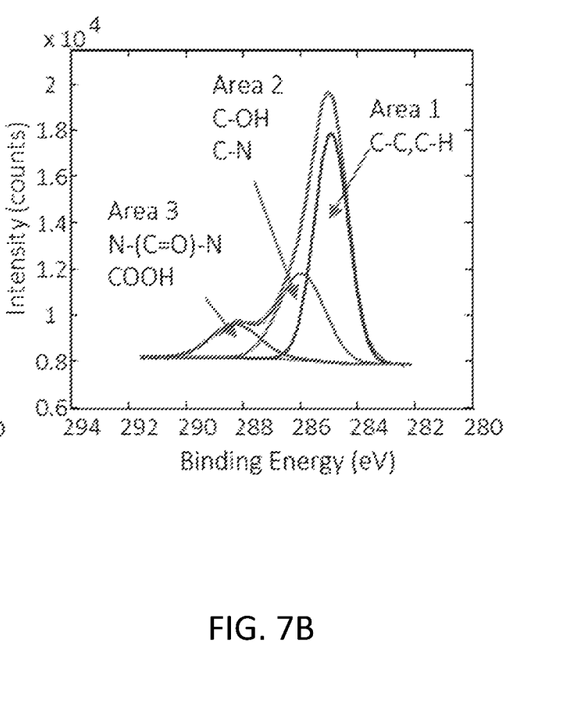
FIG. 7B shows the C1s after streptavidin functionalization. The increase in area 3 suggests the successful attachment of streptavidin to the surface.
Figure 8A:
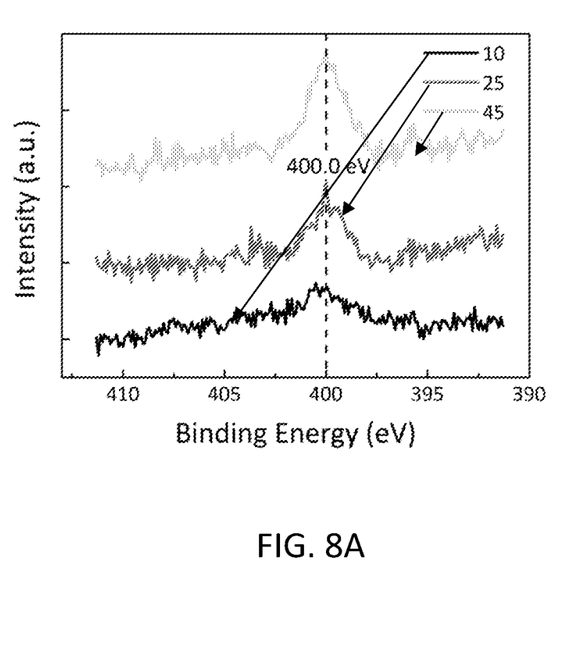
FIG. 8A depicts the increment of the N1s peak before streptavidin attachment under different takeoff angles.
Figure 8B:
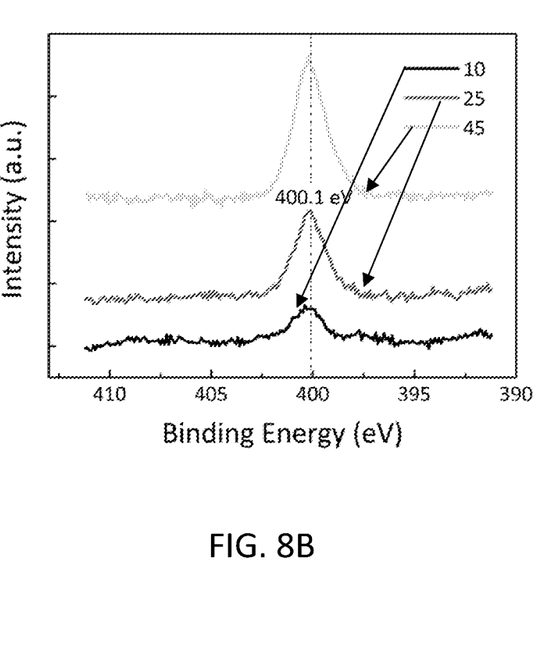
FIG. 8B depicts the increment of the N1s peak after streptavidin attachment under different takeoff angles.
Figure 9:
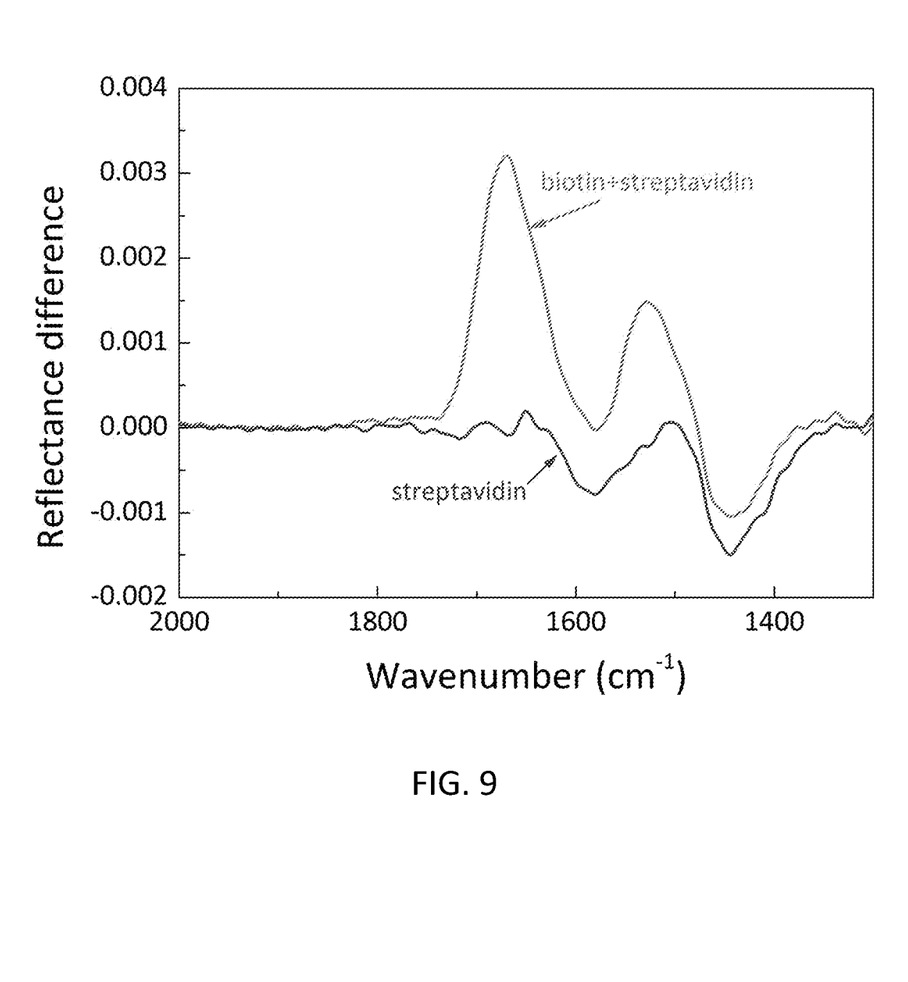
FIG. 9 shows the reflectance changes upon surface functionalization with biotin and streptavidin. The ITO glass functionalized with phosphonic-acid derived biotin shows higher signal, indicating stronger specific bonding between biotin and streptavidin.

Biotin and streptavidin show strong mutual attraction that has been widely utilized for immobilization of various functional biomolecules, such as proteins, and enzymes, onto solid substrates. Therefore, streptavidin-functionalized substrates can create a strong foundation for numerous biological studies and sensing applications. Here, the aim was to achieve streptavidin-functionalized ITO nanorod arrays for further SEIRA applications. The attachment of streptavidin to biotin-functionalized surface was first confirmed using ITO glasses with XPS measurements (FIGS. 7 and 8). Furthermore, infrared reflection absorption spectroscopy (IRRAS) was performed (FIG. 9), showing the specific bonding between biotin and streptavidin. To demonstrate the reliable attachment of streptavidin, it was necessary to chemically functionalize the ITO nanorod surface with phosphonic-acid-derived biotin molecules. As expected, direct physical adsorption of streptavidin to the ITO surfaces was not observed in these experiments. Phosphonic acid-based surface functionalization of ITO nanorod was shown to provide an effective and reliable means to functionalize the ITO nanorods for biosensing applications.

Figure 4A:
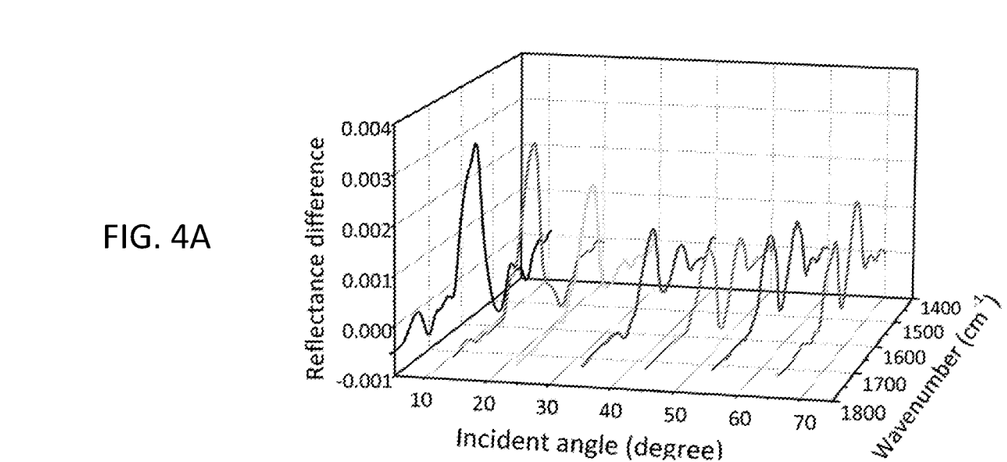
FIG. 4A shows the reflectance difference signals of the streptavidin molecules on ITO nanorods under different incident angles in a perspective view.
Figure 4B:
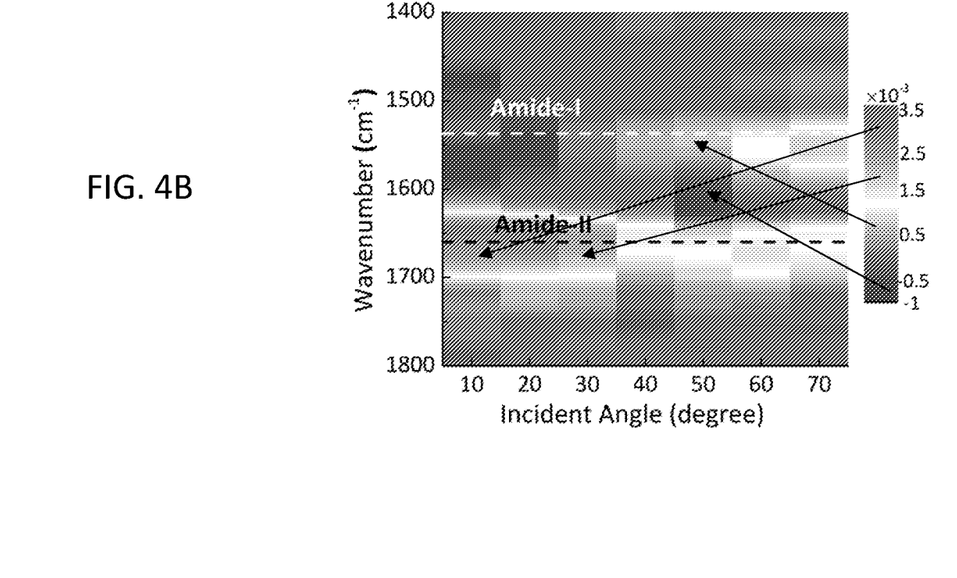
FIG. 4B shows the reflectance difference signals of the streptavidin molecules on ITO nanorods under different incident angles in a 2D map.

After streptavidin was attached to the surface, the reflectance spectra were taken under different incident angles, and the spectral ranges of interest (1800~1400 $cm^{-1}$) were fitted with $3^{rd}$ order polynomials. The difference between the fitting and the spectra were analyzed, and the results were shown in FIG. 4. Vibration signals of the Amide-I (1660 $cm^{-1}$) and Amide-II (1537 $cm^{-1}$) from the streptavidin were clearly observed on all the difference spectra with varying signal strength. At near-normal incidence, only Amide-I, which resulted from the stretch vibration of the carbonyl bond in amide, was observed. As the incident angle increased, the intensity of Amide-I band became smaller while the Amide-II band, which resulted from the NH bending in amide, grew and eventually exhibited a stronger intensity than the Amide-I band, as indicated in FIG. 4B. This evolving behavior of the spectrum was consistent with previous observations of the two plasmon modes of the ITO nanorod array in FIG. 2, which showed that mode I (at higher wavenumber) was stronger at smaller incident angles, while mode II (at lower wavenumber) was stronger at larger incident angles. Thus, selective enhancement of the two amide bands was achieved by varying the incident angle of the electromagnetic waves. Varying the incident angle provided an effective method to actively tune the frequencies of the plasmon resonances of periodically arranged 3D nanostructures. It did not require any stimuli-responsive materials in the device and was readily carried out without complexity. Such selective plasmonic enhancement can be useful for monitoring multiple vibrational signals in infrared biosensing applications. With our successful protein functionalization and subsequent sensing of streptavidin, various types of plasmonic ITO nanoantenna arrays could be applied for the detection of a wide range of biomolecules and proteins via SEIRA.

In conclusion, the use of single-crystal ITO nanorods and their protein functionalization for surface-enhanced infrared spectroscopy for biomolecule detection have been demonstrated. The ITO nanorods were surface functionalized with phosphonic-acid-derived biotin molecules and, subsequently, streptavidin. Both the XPS and infrared spectroscopy measurements confirmed the successful functionalization of ITO surfaces and the subsequent attachment of biomolecules. In addition, it was shown that the plasmon modes of the ITO nanorod array could be effectively tuned, in terms of both intensity and resonance wavelength, by varying the incident angles. Selective enhancement of the two amide bands from streptavidin was achieved by changing the incident angles. It is noted that the 3D vertical configuration of the ITO nanorods allowed for more accessible enhanced near-field and robust immobilization of large biomolecules and cells. Together with their plasmonic response in the infrared range, ITO nanorods can provide additional advantages for nanoscale investigation of intracellular delivery and biosensing of cellular activities with both spatial and spectral information. Thus, periodic ITO nanostructures with robust surface functionalization provide a new and powerful approach for biomolecule sensing by using infrared spectroscopy.

EXPERIMENTAL SECTION

Fabrication.

A large area of periodic ITO arrays (9 mm×6 mm) was fabricated with the method outlined in Li et al., *ACS Nano* 2011, 5, 9161. An epitaxial indium tin oxide film of ~10 nm thickness was grown on a YSZ (100) substrate using magnetron sputtering (target from Kurt J. Lesker) at 600° C., under 20 sccm Ar (ultra-high-purity) flow at a pressure of 5 mTorr. A GL-2000 high resolution electron beam resist was then spin-coated onto the substrate with a thickness of 70 nm. Large-area periodic dots (150 nm in diameter) were patterned using a 100 kV electron beam lithography system (JEOL 9300). Development was performed in Xylene at room temperature for 60 seconds. A 2 nm chromium (adhesion layer) and 15 nm gold (catalyst layer) were thermally evaporated onto the substrate, followed by lift-off in Anisole at 75° C. for one hour, resulting in a gold nanoparticle array on an ITO film/YSZ substrate. The nanorod growth was performed in a tube-furnace system, with a solid precursor (In and SnO, molar ratio 9:1, 100 mg total weight) temperature of 900° C. and substrate temperature of 840° C. During the growth, 6 sccm 5% $O_2$ (balanced by ultra-high-purity $N_2$) and 80 sccm ultra-high-purity Ar were flowed through the tube at a pressure of 130 mTorr (measured at the exhaust).

Figure 10:
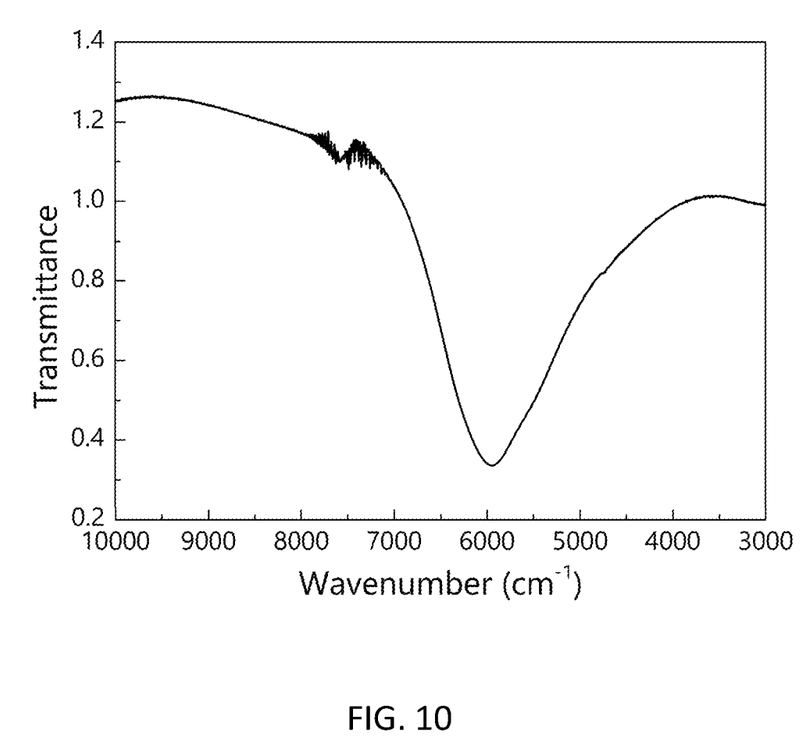
FIG. 10 depicts the transmittance spectrum of the ITO nanorod arrays under normal incidence with unpolarized light. The dip in the spectrum is due to the excitation of the transverse mode of the nanorods.

Using the resonance frequency of the transverse mode of the ITO nanorods (FIG. 10), which corresponds to the quasi-static limit of the plasmon resonance condition and the Drude model for ITO, the plasma frequency of the ITO nanorods was estimated at ~1.84 eV, and the electron concentration was estimated at ~$7.4 \times 10^{20}$ $cm^{-3}$.

Surface Functionalization.

ITO glass substrates were cleaned using an ultrasonication bath at room temperature in acetone, ethanol, and deionized water for five minutes each. Subsequently, the samples were cleaned under UV-ozone environment for 5 min (Fliegen Inc., UV-Ozone cleaner UV253). The ITO nanorod arrays were only exposed to ozone cleaning to avoid any possible damage from the strong ultrasonication before being dipped in phosphonic-acid-derived biotin solutions (20 mL, 0.05 µM in ethanol) for surface functionalization (24 hours). The biotin molecules were purchased from Dojindo Molecular Technologies, Inc. The samples were then rinsed with ethanol and water and dried using $N_2$ gas. Finally, the samples were dipped in streptavidin solution for 1 hour (100 µg/mL in PBS, pH=7.4), followed by a PBS buffer and copious DI water rinsing. Finally, the samples were dried using $N_2$ gas.

Characterization.

X-ray photoelectron spectroscopy (XPS) analysis was performed in a Quantera SXM model (ULVAC-PHI Inc.) in the standard configuration. Spectra were acquired using a monochromatic Al Kα X-ray source operating at 100 W at a base pressure of $10^{-7}$ Pa. The measurements were conducted at several takeoff angles (10°, 25°, and 45°) with respect to the surface normal.

The ITO nanorod arrays were characterized with a conventional FTIR spectrometer (Nicolet iS50R, Thermo Fisher Scientific Inc.). Reflectance spectra were collected using a modified variable angle reflectance accessory (Harrick Scientific) with a liquid nitrogen-cooled mercury cadmium telluride (MCT) detector. P-polarized light was focused onto the samples by a parabolic mirror to excite the longitudinal plasmon resonances of the ITO nanorods, and a gold mirror (100 nm in thickness) was used as reference. To measure the transverse modes of the ITO nanorods, a transmission setup was used with normal incidence and unpolarized light. Since the transverse modes were expected in the near infrared (NIR) range, white light was used as source instead and the transmitted light in air was used as reference.

Simulation.

The electric field distribution of ITO rod array was carried out using finite-difference time-domain (FDTD) method (FULLWave, Rsoft). The optical properties of ITO and YSZ were taken from Li et al., *ACS Nano* 2011, 5, 9161. A plasma frequency of 1.84 eV was used for the ITO based on the estimation. In the simulation, the incident electromagnetic field propagated along the −z axis at a 50° angle to the surface normal (the same as the longitudinal direction of the ITO nanorods), and the electric field propagated in the xz plane. A grid size of 5 nm was chosen for the simulation domain. A perfectly matched layer boundary condition was applied to the z axis, and a periodic boundary condition was applied to both x and y axes. The incident electric field amplitude was normalized to unity.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A substrate for surface-enhanced spectroscopy comprising
   (a) a substrate; and
   (b) an array of nanostructures on the substrate, wherein the nanostructures are functionalized with specific binding moieties that are bound to the nanostructures via phosphonic acid linkers,
   wherein the nanostructures comprise an electrically conductive oxide that is not titanium oxide, aluminum oxide, or zinc oxide, an electrically conductive nitride, an electrically conductive boride, an electrically conductive carbide, or a non-noble metal that is not titanium, aluminum, or zinc.

2. The substrate of claim 1, wherein phosphonic acid linkers comprise the structure -R—P(OH)$_3$, wherein R represents a single bond or a spacer comprising at least a carbon and hydrogen.

3. The substrate of claim 2, wherein R is an alkyl group, an alkoxyl group or a thioalkyl group.

4. The substrate of claim 2, wherein specific binding moieties are bound to the R groups of the phosphonic acid linkers.

5. The substrate of claim 1, wherein the nanostructures comprise electrically conductive metal oxide nanoparticles.

6. The substrate of claim 5, wherein the nanostructures comprise indium-tin-oxide.

7. The substrate of claim 1, wherein the nanostructures have a native surface oxide layer and the phosphonic acid linkers are bound to the native surface oxide.

8. The substrate of claim 1, wherein the nanostructures comprise TiN, ZrN, TaN, HfN, or doped GaN.

9. The substrate of claim 1, wherein the nanostructures comprise TiC, TaC, NbC, HfC, or doped SiC.

10. The substrate of claim 1, wherein the nanostructures comprise LaB$_6$, PrB$_6$, CeB$_6$, AlB$_2$, or ZrB$_2$.

11. The substrate of claim 1, wherein the nanostructures comprise Fe, Ta, Pt, Ir, Cu, W, or Mo.

12. The substrate of claim 1, wherein the nanostructures are plasmonic nanostructures.

13. The substrate of claim 12, wherein the nanostructures comprise indium-tin-oxide, Al, Ga-doped ZnO, or Ga-doped InO.

14. The substrate of claim 1, wherein the nanostructures are polaritonic nanostructures.

15. The substrate of claim 14, wherein the nanostructures comprise SrTiO$_3$, Ta$_2$O$_3$, BaTiO$_3$, Si or Ge.

16. The substrate of claim 1, wherein the specific binding moieties are biomolecules.

17. The substrate of claim 16, wherein the specific binding moieties comprise proteins, single-stranded DNA, polypeptides, or a combination thereof.

18. The substrate of claim 1, wherein the specific binding moieties comprise crown ether molecules.

19. A substrate for surface-enhanced spectroscopy comprising
(a) a substrate; and
(b) an array of nanostructures on the substrate, wherein the nanostructures are functionalized with specific binding moieties that are bound to the nanostructures via phosphonic acid linkers,
wherein the nanostructures comprise an electrically conductive oxide, an electrically conductive nitride, an electrically conductive boride, an electrically conductive carbide, or a non-noble metal, wherein specific binding moieties are bound directly to the P atoms of the phosphonic acid linkers.

20. The substrate of claim 19, wherein the specific binding moieties are biomolecules.

21. The substrate of claim 20, wherein the specific binding moieties comprise proteins, single-stranded DNA, polypeptides, or a combination thereof.

22. The substrate of claim 19, wherein the specific binding moieties comprise crown ether molecules.

23. The substrate of claim 19, wherein the specific binding moieties comprise dioxin molecules.

24. A substrate for surface-enhanced spectroscopy comprising
(a) a substrate; and
(b) an array of nanostructures on the substrate, wherein the nanostructures are functionalized with specific binding moieties that are bound to the nanostructures via phosphonic acid linkers,
wherein the nanostructures comprise an electrically conductive oxide, an electrically conductive nitride, an electrically conductive boride, an electrically conductive carbide, or a non-noble metal, wherein the specific binding moieties comprise dioxin molecules.

25. A method of conducting surface-enhanced spectroscopy using:
(a) a substrate; and
(b) an array of nanostructures on the substrate, wherein the nanostructures are functionalized with specific binding moieties that are bound to the nanostructures via phosphonic acid linkers,
wherein the nanostructures comprise an electrically conductive oxide that is not titanium oxide, aluminum oxide, or zinc oxide, an electrically conductive nitride, an electrically conductive boride, an electrically conductive carbide, or a non-noble metal that is not titanium, aluminum, or zinc, the method comprising:
exposing the array of nanostructures to a sample containing, or suspected of containing, analyte molecules that undergo specific binding reactions with the specific binding moieties;
irradiating the array of nanostructures with incident radiation; and
measuring a signal produced by the bound analyte molecules.

26. The method of claim 25, further comprising comparing the measured signal with a database of signals and identifying the analytes in the sample based on the comparison.

27. The method of claim 25, wherein the surface-enhanced spectroscopy is surface-enhanced infrared absorption spectroscopy, the incident radiation is infrared radiation, and the measured signal is an absorption signal.

* * * * *